US008796184B2

(12) United States Patent
Chilkoti et al.

(10) Patent No.: US 8,796,184 B2
(45) Date of Patent: Aug. 5, 2014

(54) DETECTION ASSAY DEVICES AND METHODS OF MAKING AND USING THE SAME

(75) Inventors: Ashutosh Chilkoti, Durham, NC (US); Angus Hucknall, Durham, NC (US)

(73) Assignee: Sentilus, Inc., Durham, NC (US)

( * ) Notice: Subject to any disclaimer, the term of this patent is extended or adjusted under 35 U.S.C. 154(b) by 866 days.

(21) Appl. No.: 12/405,300

(22) Filed: Mar. 17, 2009

(65) Prior Publication Data

US 2009/0247424 A1    Oct. 1, 2009

Related U.S. Application Data

(60) Provisional application No. 61/040,223, filed on Mar. 28, 2008.

(51) Int. Cl.
*C40B 40/00* (2006.01)
*C40B 40/08* (2006.01)
*C40B 40/10* (2006.01)
*C40B 30/04* (2006.01)

(52) U.S. Cl.
USPC .......... 506/13; 506/9; 506/17; 506/18; 435/4; 435/6.1; 435/7.1

(58) Field of Classification Search
USPC .................. 435/4, 6.1, 7.1; 506/9, 13, 17, 18
See application file for complete search history.

(56) References Cited

U.S. PATENT DOCUMENTS

| | | |
|---|---|---|
| 5,582,981 A | 12/1996 | Toole et al. |
| 5,840,867 A | 11/1998 | Toole et al. |
| 6,413,587 B1 | 7/2002 | Hawker et al. |
| 6,423,465 B1 | 7/2002 | Hawker et al. |
| 6,444,254 B1 | 9/2002 | Chilkoti et al. |
| 6,512,060 B1 | 1/2003 | Matyjaszewski et al. |
| 6,541,580 B1 | 4/2003 | Matyjaszewski et al. |
| 6,582,926 B1 | 6/2003 | Chilkoti |
| 6,649,138 B2 | 11/2003 | Adams et al. |
| 6,815,078 B2 | 11/2004 | Qiao et al. |
| 6,867,289 B1 | 3/2005 | Gorenstein et al. |
| 6,884,628 B2 | 4/2005 | Hubbell et al. |
| 2002/0031776 A1 | 3/2002 | Tullis et al. |
| 2003/0059537 A1 | 3/2003 | Chilkoti |
| 2003/0082604 A1* | 5/2003 | Swanson et al. .................. 435/6 |
| 2003/0108879 A1 | 6/2003 | Klaerner et al. |
| 2003/0143535 A1 | 7/2003 | Lyamichev et al. |
| 2003/0185741 A1 | 10/2003 | Matyjaszewski et al. |

(Continued)

OTHER PUBLICATIONS

Dai et al. (High-capacity binding of proteins by poly(acrylic acid) brushes and their derivatives, 2006, Langmuir, vol. 22, pp. 4274-4281).*

(Continued)

*Primary Examiner* — Sharmila G. Landau
*Assistant Examiner* — Shannon Janssen
(74) *Attorney, Agent, or Firm* — Wilson Sonsini Goodrich & Rosati, PC

(57) ABSTRACT

An article such as a biomolecular detector or biosensor having a nonfouling surface thereon includes: (a) a substrate having a surface portion; (b) a linking layer on the surface portion; and (c) a polymer layer formed on the linking layer; and (d) a first member of a specific binding pair (e.g., a protein, peptide, antibody, nucleic acid, etc.) bound to the polymer layer. Methods of making and using the articles are also described.

24 Claims, 4 Drawing Sheets

(56) References Cited

U.S. PATENT DOCUMENTS

| | | | |
|---|---|---|---|
| 2004/0197899 A1 | 10/2004 | Gomez et al. | |
| 2004/0242023 A1 | 12/2004 | Yan et al. | |
| 2005/0079598 A1* | 4/2005 | Davis | 435/287.1 |
| 2005/0100987 A1 | 5/2005 | Evans et al. | |
| 2005/0164205 A1 | 7/2005 | Puskas | |
| 2005/0282242 A1 | 12/2005 | Rothstein et al. | |
| 2006/0057180 A1 | 3/2006 | Chilkoti et al. | |
| 2008/0311681 A1* | 12/2008 | Johannsen et al. | 436/548 |
| 2010/0099579 A1* | 4/2010 | Chilkoti | 506/16 |

OTHER PUBLICATIONS

International Search Report and Written Opinion, PCT/US06/36102, Aug. 6, 2007.

Kane R S et al. Kosmotropes Form the Basis of Protein-Resistant Surfaces. Langmuir (2003), vol. 19, pp. 2388-2391.

Ma H et al. "Non-Fouling" Oligo(ethylene glycol)-Functionalized Polymer Brushes Synthesized by Surface-Initiated Atom Transfer Radical Polymerization. Advanced Materials (Feb. 17, 2004), vol. 16, No. 4, pp. 338-341.

Nath N et al. Surface engineering strategies for control of protein and cell interactions. Surface Science (2004), vol. 570, pp. 98-110.

Ishihara et al., Photoinduced graft polymerization of 2-methacryloyloxyethl phosphorylcholine on polyethylene membrane surface for obtaining blood cell adhesion resistance, Colloids and Surfaces B: Biointerfaces, (2000), pp. 325-335, 18.

Kim et al., Surface-Initiated Atom Transfer Radical Polymerization on Gold at Ambient Temperature, Journal of the American Chemical Society, (2000), pp. 7616-7617, 122.

* cited by examiner

DETECTION ASSAY DEVICES AND METHODS OF MAKING AND USING THE SAME

RELATED APPLICATIONS

This application claims the benefit of Ashutosh Chilkoti and Angus Hucknall, U.S. Provisional Patent Application Ser. No. 61/040,223, filed Mar. 28, 2008, the disclosure of which is incorporated by reference herein in its entirety.

This application is related to Ashutosh Chilkoti, Non-fouling polymeric surface modification and signal amplification method for biomolecular detection, US Patent Application Pub. No. US 2007/0072220, published Mar. 29, 2007 (U.S. patent application Ser. No. 11/521,651) (also published as PCT Application No. WO 2007/035527 on Mar. 29, 2007), now U.S. Pat. No. 7,713,689, the disclosure of which is incorporated by reference herein in its entirety.

FIELD OF THE INVENTION

This invention relates to devices for biomolecular detection.

BACKGROUND OF THE INVENTION

Microarrays are a powerful and established tool in genomics.[1] In contrast, the development of antibody (Ab) microarrays into an equivalent tool for proteomics has been limited by: (1) the availability of high affinity and specificity antibodies for capture and detection of protein biomarkers; (2) the susceptibility of proteins to denaturation; and (3) the propensity of Ab's and protein biomarkers to avidly adsorb to surfaces (commonly referred to as the "non-specific adsorption" problem), which can severely limit the ultimate sensitivity of protein microarrays, especially from complex protein mixtures such as plasma and serum.[2] One of the primary factors (others include the intrinsic affinity of the capture antibody and the diffusion of target to the microspot[2,3]) that controls the limit-of-detection (LOD) of protein microarrays is the adventitious adsorption of proteins (protein biomarkers and antibodies used for detection).

SUMMARY OF THE INVENTION

A first aspect of the present invention is an article (preferably a biomolecular detector or biosensor such as a microarray) having a nonfouling surface thereon, the article comprising:

(a) a substrate having a surface portion;
(b) a linking layer on the surface portion; and
(c) a polymer layer formed on the linking layer (e.g., by the process of surface-initiated polymerization (SIP) of monomeric units thereon). Preferably, each of the monomeric units comprises a monomer (for example, a vinyl monomer) core group having at least one protein-resistant head group coupled thereto, to thereby form a brush molecule on the surface portion. The brush molecule preferably comprises a stem formed from the polymerization of the monomer core groups, and a plurality of branches formed from the head group projecting from the stem; and
(d) a first member of a specific binding pair (e.g., a protein, peptide, antibody, nucleic acid, etc.) non-covalently bound to the polymer layer.

A second aspect of the present invention is a method of making an article (preferably a biomolecular detector such as a microarray) having a nonfouling surface thereon, the method comprising: (a) providing a substrate having a surface portion; (b) depositing a linking layer on the surface portion; and (c) forming a polymer layer on the linking layer by the process of surface-initiated polymerization of monomeric units thereon, with each of the monomeric units comprising a monomer (for example, a vinyl monomer) core group having at least one protein-resistant head group coupled thereto, to thereby form a brush molecule on the surface portion; the brush molecule comprising a stem formed from the polymerization of the monomer core groups, and a plurality of branches formed from the hydrophilic head group projecting from the stem; and then (d) non-covalently binding a member of a specific binding pair to the polymer layer.

In some embodiments the polymer comprises a homopolymer of hydroxy-terminated OEGMA. In another embodiment the polymer comprises of a copolymer of methoxy-terminated OEGMA and hydroxy-terminated OEGMA. In other embodiments the polymer comprises of vinyl monomer bearing other head groups such as hydroxyl (OH), glycerol, or groups known in the art as kosmotropes (see, e.g., Kane et al., infra).

In some embodiments of the invention, the surface portion comprises a material selected from the group consisting of metals, metal oxides, semiconductors, polymers, silicon, silicon oxide, and composites thereof.

In some embodiments of the invention the linking layer is continuous; in some embodiments of the invention the linking layer is patterned. In some embodiments of the invention the linking layer is a self-assembled monolayer (SAM). In some embodiments of the invention the linking layer comprises an initiator-terminated silane or an initiator-terminated alkanethiol. In other embodiments the linking layer comprises of the deposition of two layers in separate steps. In the first step, an alkylsilane or alkanethiol is deposited on a surface such as silicon dioxide or glass or gold, and presents a terminal reactive functional group (e.g., amine). In the next step, a bifunctional molecule, which comprises a first functional group reactive towards the terminal group presented by the first linking layer is reacted with the first linking layer deposited in the first step. The second linker molecule contains a second moiety group that acts as an ATRP or free radical initiator.

In some embodiments of the invention the surface-initiated polymerization is carried out by atom transfer radical polymerization (ATRP); in some embodiments of the invention the surface-initiated polymerization is carried out by free radical polymerization.

In some embodiments, the article further comprises a protein, peptide, oligonucleotide or peptide nucleic acid non-covalently bound to the polymer layer. In some embodiments the protein, peptide, oligonucleotide or peptide nucleic acid coupled to the polymer layer or to the surface consists of or consist essentially of a single preselected molecule (this is, one such molecule is coupled to the surface portion via the brush molecule, to the exclusion of other different molecules). The preselected molecule may be a member of a specific binding pair, such as a receptor.

A further aspect of the invention is a method of detecting a second member of a specific binding pair in a sample, comprising the steps of: (a) providing a detector as described herein; (b) contacting a sample (e.g., an aqueous sample or biological fluid) suspected of containing the second member(s) to the detector; and then (c) determining the presence or absence of binding of the second member to the first member, the presence of binding indicating the presence of the second member in the sample. The determining step can be carried out by any suitable technique, such as by sandwich assay, as discussed further below.

Arrays.

In some embodiments of the foregoing methods and devices, useful for the detection of multiple different analytes, the first member of said specific binding pair is non-covalently bound to said polymer at a discrete probe location, and the biomolecular detector further comprises: (e) a plurality of additional first members of a specific binding pairs non-covalently bound to said polymer layer at a plurality of additional discrete probe locations to thereby form an array thereon. In some embodiments the array has a density of 5 to 10,000 discrete probe locations per $cm^2$ thereon; in some embodiments the array has a density of 10,000 to 1 million discrete probe locations per $cm^2$ thereon; and in some embodiments the array has a density of 1 million to 1 billion discrete probe locations per $cm^2$ thereon.

An advantage of the foregoing methods is the variety of techniques by which the detecting step can be carried out. For example, the detecting step may be carried out by: (a) ellipsometry; (b) surface plasmon resonance (SPR); (c) localized surface plasmon resonance using noble metal nanoparticles in solution or on a transparent surface; (d) surface acoustic wave (SAW) devices; (e) quartz-crystal microbalance with dissipation (QCM-D) (e) atomic force microscopy, (f) fluorescence spectroscopy or imaging; (g) autoradiography, (h) chemiluminescent imaging; and (i) optical detection of metal nanoparticles either by extinction or scattering, etc.

Still other aspects of the present invention are explained in greater detail below.

DETAILED DESCRIPTION OF THE PREFERRED EMBODIMENTS

Figure 1:
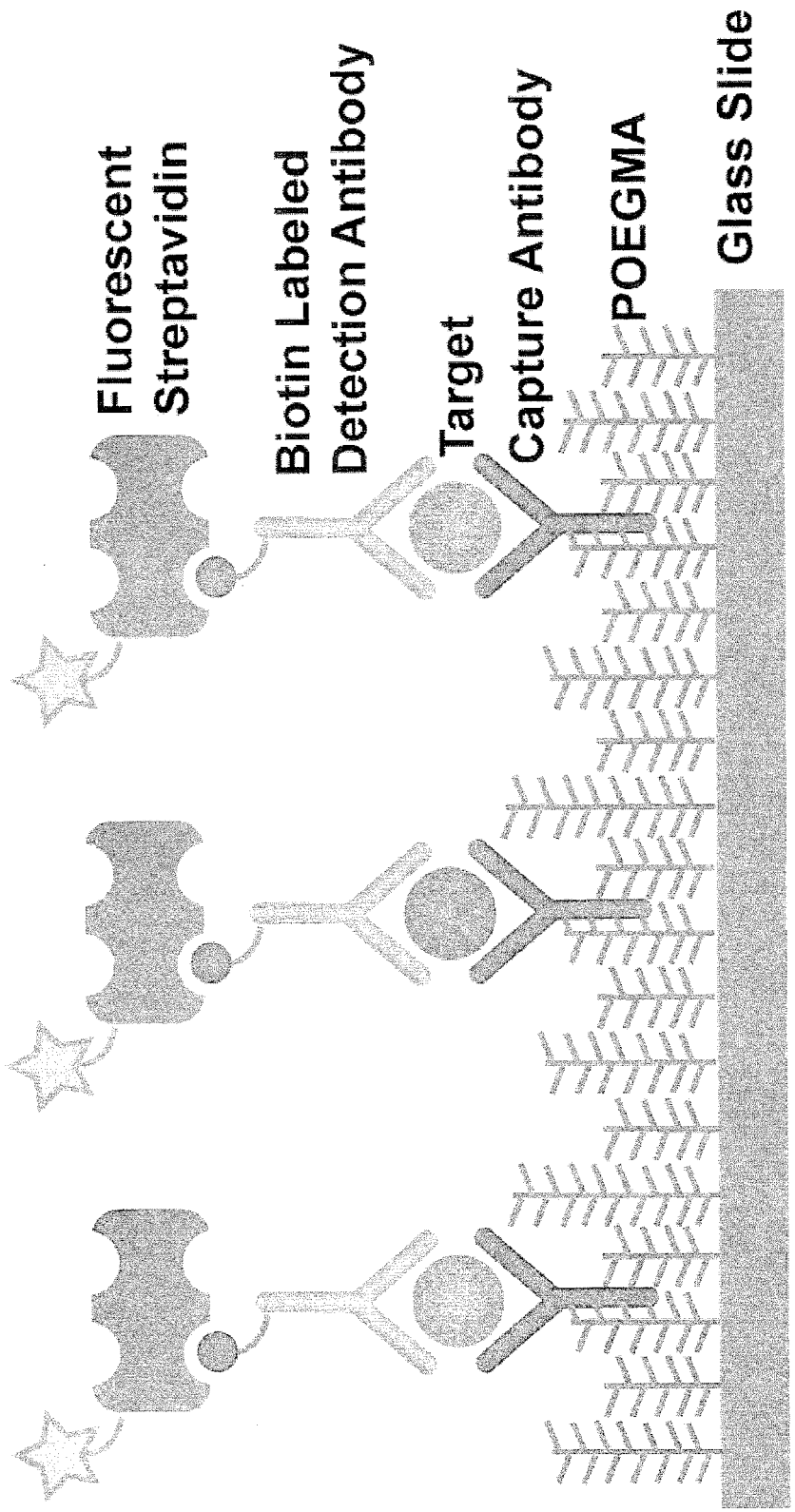
FIG. 1. A schematic diagram of an array of the present invention.

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs.

The disclosures of all United States patents cited herein are incorporated by reference in their entirety.

1. Definitions

"SI-ATRP" as used herein means surface initiated atom transfer radical polymerization.

"OEGMA" as used herein refers to oligo(ethylene glycol) methyl methacrylate.

"Biological fluid" as used herein may be any fluid of human or animal origin, including but not limited to blood, blood plasma, serum, peritoneal fluid, cerebrospinal fluid, tear, mucus, lymph fluid, semen, saliva, urine, lavage fluid from a wound or bodily orifice, etc. Biological fluids generally contain a mixture of a plurality of different proteins therein, and typically contain other constituents such as other cells and molecules. Biological fluids may be in their natural state or in a modified state by the addition of ingredients such as reagents or removal of one or more natural constituents (e.g., blood plasma), but all typically comprise a mixture of a plurality of different potential analytes, such as a plurality of different proteins.

"Kosmotrope", while originally used to denote a solute that stabilized a protein or membrane, is also used by those skilled in the art, and is used herein, to denote a substituent or "head group" which, when deposited on a surface, renders that surface protein-resistant. See, e.g., R. Kane, P. Deschatelets and G. Whitesides, *Kosmotropes Form the Basis of Protein-Resistant Surfaces, Langmuir* 19, 2388-2391 (2003). Numerous kosmotropes are known and examples include but are not limited to OEGMA.

"Polymer" as used herein is intended to encompass any type of polymer, including homopolymers, heteropolymers, co-polymers, ter-polymers, etc., and blends, combinations and mixtures thereof.

"Specific binding pair" as used herein refers to two compounds that specifically bind to one another, such as (functionally): a receptor and a ligand (such as a drug), an antibody and an antigen, etc.; or (structurally): protein or peptide and protein or peptide; protein or peptide and nucleic acid; and nucleotide and nucleotide etc. "Nucleic acids" may be any natural or synthetic nucleic acids, including DNA and RNA, and are typically from 10 to 1,000 nucleotides in length. Typically the first member of the specific binding pair (or "probe") is a protein, peptide or nucleic acid that specifically binds to the second member (or "analyte") to be detected.

"Analyte" as used herein may be any second member of a specific binding pair, as described above. Typically the analyte is a constituent or found in a biological fluid as described herein. Examples of such analytes include, but are not limited to: thyroid stimulating hormone, glycosylated hemoglobin, parathormone, prostate-specific antigen (psa), ferritin, natriuretic peptide, folic acid, hepatitis b surface antigen, blood lipoproteins, vitamin D, carcinoembryonic antigen, nuclear antigen antibody, testosterone, homocystine, HIV-1 DNA, ck (cpk) gammaglobulin, etc. The analyte can be a "marker" protein, peptide or other molecule specifically found in patients infected or afflicted with a microbial infection, examples of which include but are not limited to Anthrax, Avian influenza, Botulism, Buffalopox, Chikungunya, Cholera, Coccidioidomycosis, Creutzfeldt-Jakob disease, Crimean-Congo haemorrhagic fever, Dengue fever, Dengue haemorrhagic fever, Diphtheria, Ebola haemorrhagic fever, Ehec (*E. Coli* 0157), Encephalitis, Saint-Louis, Enterohaemorrhagic *escherischia coli* infection Enterovirus, Foodborne disease, Haemorrhagic fever with renal syndrome, Hantavirus pulmonary syndrome, Hepatitis, Influenza, Japanese encephalitis, Lassa fever, Legionellosis, Leishmaniasis, Leptospirosis, Listeriosis, Louseborne typhus, Malaria, Marburg haemorrhagic fever, Measles, Meningococcal disease, Monkeypox, Myocarditis Nipah virus, O'Nyong-Nyong fever, Pertussis, Plague, Poliomyelitis, Rabies, Relapsing fever, Rift Valley fever, Severe acute respiratory syndrome (SARS), Shigellosis, Smallpox vaccine—accidental exposure, Staphylococcal food intoxication, Tularaemia, Typhoid fever, West Nile fever, Yellow fever, etc. The analyte can be a "marker" protein, peptide or other molecule specifically found in patients infected or afflicted with a fungal infection, or viral infection. In all of the preceding examples, the analyte may be derived from the infectious agent itself, namely microbe, fungus or virus, or may be proteins or other biomarkers (such as lipids, carbohydrates or DNA) that are found in greater or lesser abundance in afflicted individuals as compared to healthy individuals.

2. Substrates

The present invention can be utilized to form surfaces on a variety of different types of substrates.

In some embodiments, the article is a label-free optical or mass detector (e.g., a surface plasmon resonance energy detector, an optical wave guide, an ellipsometry detector, etc.) and the surface is a sensing surface (e.g., a surface portion that would be in contact with a biological fluid). Examples of such articles include but are not limited to those described in U.S. Pat. Nos. 6,579,721; 6,573,107; 6,570,657; 6,423,055; 5,991,048; 5,822,073; 5,815,278; 5,625,455; 5,485,277; 5,415,842; 4,844,613; and 4,822,135.

In other embodiments, the article is a biosensor, an assay plate, or the like. For example, the present invention may be utilized with optical biosensors such as described in U.S. Pat. No. 5,313,264 to Ulf et al., U.S. Pat. No. 5,846,842 to Herron et al., U.S. Pat. No. 5,496,701 to Pollard-Knight et al., etc. The present invention may be utilized with potentiometric or electrochemical biosensors, such as described in U.S. Pat. No. 5,413,690 to Kost, or PCT Application WO98/35232 to Fowlkes and Thorp. The present invention may be utilized with a diamond film biosensor, such as described in U.S. Pat. No. 5,777,372. Thus, the solid support may be organic or inorganic; may be metal (e.g., copper or silver) or non-metal; may be a polymer or nonpolymer; may be conducting, semiconducting or nonconducting (insulating); may be reflecting or nonreflecting; may be porous or nonporous; etc. For example, the solid support may be comprised of polyethylene, polytetrafluoroethylene, polystyrene, polyethylene terephthalate, polycarbonate, gold, silicon, silicon oxide, silicon oxynitride, indium, tantalum oxide, niobium oxide, titanium, titanium oxide, platinum, iridium, indium tin oxide, diamond or diamond-like film, etc.

The present invention may be utilized with substrates for "chip-based" and "pin-based" combinatorial chemistry techniques. All can be prepared in accordance with known techniques. See. e.g., U.S. Pat. No. 5,445,934 to Fodor et al., U.S. Pat. No. 5,288,514 to Ellman, and U.S. Pat. No. 5,624,711 to Sundberg et al., the disclosures of which are incorporated by reference herein in their entirety.

Substrates as described above can be formed of any suitable material, including but not limited to a material selected from the group consisting of metals, metal oxides, semiconductors, polymers (particularly organic polymers in any suitable form including woven, nonwoven, molded, extruded, cast, etc.), silicon, silicon oxide, and composites thereof.

Polymers used to form substrates as described herein may be any suitable polymer, including but not limited to: poly (ethylene) (PE), poly(propylene) (PP), cis and trans isomers of poly(butadiene) (PB), cis and trans isomers of poly(isoprene), poly(ethylene terephthalate) (PET), polystyrene (PS), polycarbonate (PC), poly(epsilon-caprolactone) (PECL or PCL), poly(methyl methacrylate) (PMMA) and its homologs, poly(methyl acrylate) and its homologs, poly(lactic acid) (PLA), poly(glycolic acid), polyorthoesters, poly(anhydrides), nylon, polyimides, polydimethylsiloxane (PDMS), polybutadiene (PB), polyvinylalcohol (PVA), polyacrylamide and its homologs such as poly(N-isopropyl acrylamide), fluorinated polyacrylate (PFOA), poly(ethylene-butylene) (PEB), poly(styrene-acrylonitrile) (SAN), polytetrafluoroethylene (PTFE) and its derivatives, polyolefin plastomers, and combinations and copolymers thereof, etc.

If desired or necessary, the substrate may have an additional layer such as a gold or an oxide layer formed on the relevant surface portion to facilitate the deposition of the linking layer, as discussed further below.

3. Linking (or "Anchor") Layers

Anchor layers used to carry out the present invention are generally formed from a compound comprising an anchor group coupled (e.g., covalently coupled) to an initiator (e.g., directly coupled or coupled through an intermediate linking group). The choice of anchor group will depend upon the surface portion on which the linking layer is formed, and the choice of initiator will depend upon the particular reaction used to form the brush polymer as discussed in greater detail below.

The anchoring group may be selected to covalently or non-covalently couple the compound or linking layer to the surface portion. Non-covalent coupling may be by any suitable secondary interaction, including but not limited to hydrophobic bonding, hydrogen bonding, Van der Waals interactions, ionic bonding, etc.

Examples of substrate materials and corresponding anchoring groups include, for example, gold, silver, copper, cadmium, zinc, palladium, platinum, mercury, lead, iron, chromium, manganese, tungsten, and any alloys thereof with sulfur-containing functional groups such as thiols, sulfides, disulfides (e.g., —SR or —SSR where R is H or alkyl, typically lower alkyl, or aryl), and the like; doped or undoped silicon with silanes and chlorosilanes (e.g., —SiR$_2$Cl wherein R is H or alkyl, typically lower alkyl, or aryl); metal oxides such as silica, alumina, quartz, glass, and the like with carboxylic acids as anchoring groups; platinum and palladium with nitrites and isonitriles; and copper with hydroxamic acids. Additional suitable functional groups suitable as the anchoring group include benzophenones, acid chlorides, anhydrides, epoxides, sulfonyl groups, phosphoryl groups, hydroxyl groups, phosphonates, phosphonic acids, amino acid groups, amides, and the like. See, e.g., U.S. Pat. No. 6,413,587.

Any suitable initiator may be incorporated into the anchoring group by introduction of a covalent bond at a location non-critical for the activity of the initiator. Examples of such initiators include, but are not limited to, bromoisobutyrate, polymethyl methacrylate-Cl, polystyrene-Cl, AIBN, 2-bromoisobutyrate, chlorobenzene, hexabromomethyl benzene, hexachloromethyl benzene, dibromoxylene, methyl bromoprionate. Additional examples of initiators include those initiators described in U.S. Pat. No. 6,413,587 to Hawker (particularly at columns 10-11 thereof) and those initiators described in U.S. Pat. No. 6,541,580 to Matyaszewski et al.

As noted above, a linking group or "spacer" may be inserted between the anchoring group and initiator. The linker may be polar, nonpolar, positively charged, negatively charged or uncharged, and may be, for example, saturated or unsaturated, linear or branched alkylene, aralkylene, alkarylene, or other hydrocarbylene, such as halogenated hydrocarbylene, particularly fluorinated hydrocarbylene. Preferred linkers are simply saturated alkylene of 3 to 20 carbon atoms, i.e., $—(CH_2)_4—$ where n is an integer of 3 to 20 inclusive. See, e.g., U.S. Pat. No. 6,413,587. Another preferred embodiment of the linker is an oligoethyleneglycol of 3 to 20 units, i.e., $(CH_2CH_2O)_n$ where n ranges from 3 to 20.

The anchoring layer may be deposited by any suitable technique. It may be deposited as a self-assembled monolayer. It may be created by modification of the substrate by chemical reaction (see, e.g., U.S. Pat. No. 6,444,254 to Chilkoti et al.) or by reactive plasma etching or corona discharge treatment. It may be deposited by a plasma deposition process. It may be deposited by spin coating or dip coating. It may be deposited by spray painting. It may also be deposited by deposition, printing, stamping, etc. It may be deposited as a continuous layer or as a discontinuous (e.g., patterned) layer.

In some preferred embodiments, the substrate is glass, silicon oxide or other inorganic or semiconductor material (e.g., silicon oxide, silicon nitride) and compound semiconductors (e.g., gallium arsenide, and indium gallium arsenide) used for microarray production.

In some preferred embodiments, the anchoring group is a silane or chlorosilane (e.g., $—SiR_2Cl$ wherein R is H or alkyl, typically lower alkyl, or aryl).

In some preferred embodiments, the linking layer comprises of the deposition of two layers in separate steps. In the first step, an anchoring layer of alkylsilane or alkanethiol is deposited on a surface such as silicon dioxide or glass or gold, and presents a terminal reactive functional group (e.g., amine). In the next step, a bifunctional molecule, which comprises a first functional group reactive towards the terminal group presented by the first linking layer is reacted with the first linking layer deposited in the first step. The second functional group of the bifunctional molecule contains a moiety group that acts as an ATRP or free radical initiator.

4. Brush Polymer Formation

The brush polymers are, in general, formed by the polymerization of monomeric core groups having a protein-resistant head group coupled thereto.

Any suitable core vinyl monomer polymerizable by the processes discussed below can be used, including but not limited to styrenes, acrylonitriles, acetates, acrylates, methacrylates, acrylamides, methacrylamides, vinyl alcohols, vinyl acids, and combinations thereof.

Protein resistant groups may be hydrophilic head groups or kosmotropes. Examples include but are not limited to oligosaccharides, tri(propyl sulfoxide), hydroxyl, glycerol, phosphorylcholine, tri(sarcosine) (Sarc), N-acetylpiperazine, betaine, carboxybetaine, sulfobetaine, permethylated sorbitol, hexamethylphosphoramide, an intramolecular zwitterion (for example, $—CH_2N^+(CH_3)_2CH_2CH_2CH_2SO_3^-$) (ZW), and mannitol.

Additional examples of kosmotrope protein resistant head groups include, but are not limited to:
- $-(EG)_6OH$;
- $—O(Mannitol)$;
- $—C(O)N(CH_3)CH_2(CH(OCH_3))_4CH_2OCH_3$;
- $—N(CH_3)_3{}^+Cl^-/—SO_3{}^{-Na+}$;
- $—N(CH_3)_2{}^+CH_2CH_2SO_3{}^-$;
- $—C(O)Pip(NAc)$;
- $—N(CH_3)_2{}^+CH_2CO_2{}^-$;
- $—O([Blc-\alpha(1,4)-Glc-\beta(1)-])$;
- $—C(O)(N(CH_3)CH_2C(O))_3N(CH_3)_2$;
- $—N(CH_3)_2{}^+CH_2CH_2CH_2SO_3{}^-$;
- $—C(O)N(CH_3)CH_2CH2N(CH_3)P(O)(N(CH_3)_2)_2$; and
- $—(S(O)CH_2CH_2CH_2)_3S(O)CH_3$.

See, e.g., R. Kane et al., *Langmuir* 19, 2388-91 (2003) (Table 1).

A particularly preferred protein resistant head group is poly(ethylene glycol), or "PEG", for example PEG consisting of from 3 to 20 monomeric units.

Free radical polymerization of monomers to form brush polymers can be carried out in accordance with known techniques, such as described in U.S. Pat. No. 6,423,465 to Hawker et al.; U.S. Pat. No. 6,413,587 to Hawker et al.; U.S. Pat. No. 6,649,138 to Adams et al.; US Patent Application 2003/0108879 to Klaerner et al.; or variations thereof which will be apparent to skilled persons based on the disclosure provided herein.

Atom or transfer radical polymerization of monomers to form brush polymers can be carried out in accordance with known techniques, such as described in U.S. Pat. No. 6,541,580 to Matyjaszewski et al.; U.S. Pat. No. 6,512,060 to Matyjaszewski et al.; or US Patent Application 2003/0185741 to Matyjaszewski et al., or variations thereof which will be apparent to skilled persons based on the disclosure provided herein.

In general, the brush molecules formed by the processes described herein (or other processes either known in the art or which will be apparent to those skilled in the art based upon the present disclosure), will be from 2 or 5 up to 100 or 200 nanometers in length, or more, and will be deposited on the surface portion at a density of from 10, 20 or 40 up to 100, 200 or 500 milligrams per meter$^2$, or more.

In some preferred embodiments, the polymer layer is formed by SI-ATRP of OEGMA to form a poly(OEGMA) film. In particularly preferred embodiments, the polymer layer is a functionalized poly(OEGMA) film prepared (preferably in a single step) by copolymerization of a methacrylate and methoxy terminated OEGMA.

Preparation of Substrate and Polymer Layer for Deposition.

Prior to deposition of the first member of the specific binding pair, the substrate and polymer layer are macroscopically dry or at least macroscopically dry (that is, dry to the touch or dry to visual inspection, but retaining bound water or water of hydration in the polymer layer). To enhance immobilization, it is preferable that the polymer layer retain bound water or water of hydration (or stated otherwise, that the article includes water consisting of or consisting essentially of waters of hydration, but not bulk surface water). When the substrate with polymer layer has been stored in desiccated form, this can be achieved by quickly hydrating, dipping, or contacting the polymer layer to water and then blow drying the surface (e.g., with a nitrogen or argon jet), or by simply exposing the polymer layer to ambient air for a time sufficient for water of hydration to be bound from the atmosphere by the polymer layer.

Deposition and Post-Deposition Drying.

The first member of the specific binding pair (as described above) can be deposited on the polymer layer by any suitable technique such as microprinting or microstamping, including piezoelectric or other forms of non-contact printing and direct contact quill printing.

When an array is being formed by the deposition of multiple first binding pairs, or "probes", at discrete probe locations on the polymer layer, probe densities of 1, 3, 5 or 10, up to 100 or 1000 probe locations per $cm^2$ can be made. Modern non-contact arrayers can be used in the deposition step to produce arrays having up to 1,000,000 probe locations per $cm^2$. With dip-pen nanolithography, arrays with up to 1 billion discrete probe locations per $cm^2$ can be made. It will be appreciated that the specific molecular species at each probe location can be different from the others, or that some can be the same (e.g., to provide some redundancy or control), depending upon the particular purpose of the array.

After deposition of the first member of the specific binding pair, the device is optionally but preferably dried, e.g., by mild desiccation, blow drying, lyophilization, or exposure to ambient air at ambient temperature, for a time sufficient for the article to be macroscopically dry or at least macroscopically dry as described above. Again, water of hydration may remain bound by the polymer layer even though the device is macroscopically dry. Once the device is macroscopically dry or at least macroscopically dry, it may be sealed in a container (e.g., such as an impermeable or semipermeable polymeric container) in which it can be stored and shipped to the user. Once sealed in the container, the device preferably has, in some embodiments, a shelf life of at least 2 to 4 months, and preferably up to 6 months or more, when stored at a temperature of 25° C. (e.g., without loss of more than 20, 30 or 50 percent of binding activity).

5. Uses and Applications of Articles

In some embodiments the present invention is utilized by (a) providing an article as described herein; and then (b) contacting the article to a biological fluid or other composition, containing a second member of the specific binding pair, wherein the second member of the specific binding pair binds to the surface portions. Such uses are particularly appropriate where the article is a sensor or biosensor as described in greater detail above.

Any suitable "second member" or "analyte" as described above can be detected. For example, the second member may be a compound found in or marker for:
HEP A/B/C/E, Influenza A/B
Common and Antibiotic-Resistant Cocci, TB, Syphillis
HIV, HCV, HTLV, HPV, Herpes Simplex, Chlamydia, Ghanaian, West Nile, Chlamydiazyme
CMV, Rubella, TOXO, TPHA, Lyme disease
ehrlichiosis, anaplasmosis, bartonellosis, typhus, Q fever, tickborne spotted fevers, actinomycete
Fungal infection markers:
aspergillosis, blastomycosis, candidiasis, coccidioidomycosis, cryptococcosis, histoplasmosis, *Pneumocystis carinii*

The second member may be one or more of, for example:
A human cytokine, such as IL-1α, IL-1β, IL-2, IL-4, IL-5, IL-6, IL-8, IL-10, IL-12, IL-13, IFNγ and TNFα;
A human IR chemokine, such as ENA-78, Eotaxin, GROα, IP-10, MCP-1, MDC, MIG, MIP-1α, MIP-1β, MPIF-1, RANTES and TARC
A human angiogenic factor, such as ANG-2, FGF Basic, HB-EGF, HGF, KGF, PDGF-BB, TIMP-1, Tpo, VEGF, FGF basic, HGF, PDGF-BB, VEGF; or
A cardiac marker, such as: Apo A-1, Apo B-100, Fibrinogen, Fibronectin and CRP; Acp-30, A-SAA, MPO, MMP-2 and MMP-9; AI-1 Active, NT-proBNP, P-Selectin, IL-8, IL-6, OPG, PAPP-A and RANKL; and
a diabetes and/or obesity marker, such as IGFBP-1, IGFBP-3, Prolactin, Resistin, CRP, ICAM-1, Acrp-30 and MMP-2; MMP-9, TNF-RII, VCAM-1 and E-Selectin; Leptin, IL-6, C-peptide and HG.

In one embodiment of the invention, a substrate of the invention contains a plurality (e.g., one, two or three, up to 20, 30, or 40 or more) of different first members that each bind to a different one of the foregoing second member/analytes at separate and discrete locations on the substrate polymer layer to form an array or microarray that can be used to test for a plurality of different analytes in the same biological fluid sample. The plurality of different first members (selected for the corresponding second members/analytes to which they bind) can be selected and deposited on the array to provide a "panel" test for a particular purpose, such as a human cytokine array; a human IR chemokine array; a human angiogenic factor array, a cardiac marker array, a diabetes and/or obesity marker array, a cancer array etc.

Binding of the second member of the specific binding pair (analyte) can be detected by any suitable technique. In some embodiments the analyte is detected by immunometric assay such as a sandwich assay. In some embodiments of a "sandwich" assay, a third binder, that also specifically binds to the second member of the binding pair (the "analyte"), is bound to the analyte, and the binding of that third binder is detected (e.g., by labelling of the third binder with a detectable group such as an enzyme, fluorescent group, or radioactive group). Such sandwich assays are well known. Numerous assay formats are known which can be used or adapted to carry out the present invention. See, e.g., U.S. Pat. Nos. 7,312,041; 7,270,970; 7,267,951; 7,247,500; 7,229,775; 7,202,028; 7,195,883; 7,166,469; 7,148,016, etc.

The present invention is explained in greater detail in the following non-limiting Examples.

EXPERIMENTAL

Herein, we demonstrate that eliminating background adsorption in protein microarrays can decrease the LOD by 100-fold in buffer and serum over the same protein microarrays printed on a conventional substrate (that displays high binding capacity but significant adventitious adsorption) without need for any other changes to the assay protocol. Notably, the LODs are equivalent for assays performed in either buffer or serum—typically, the LODs for most immunoassays obtained in buffer are severely compromised when complex protein mixtures such as serum are probed.[4]

Figure 2:
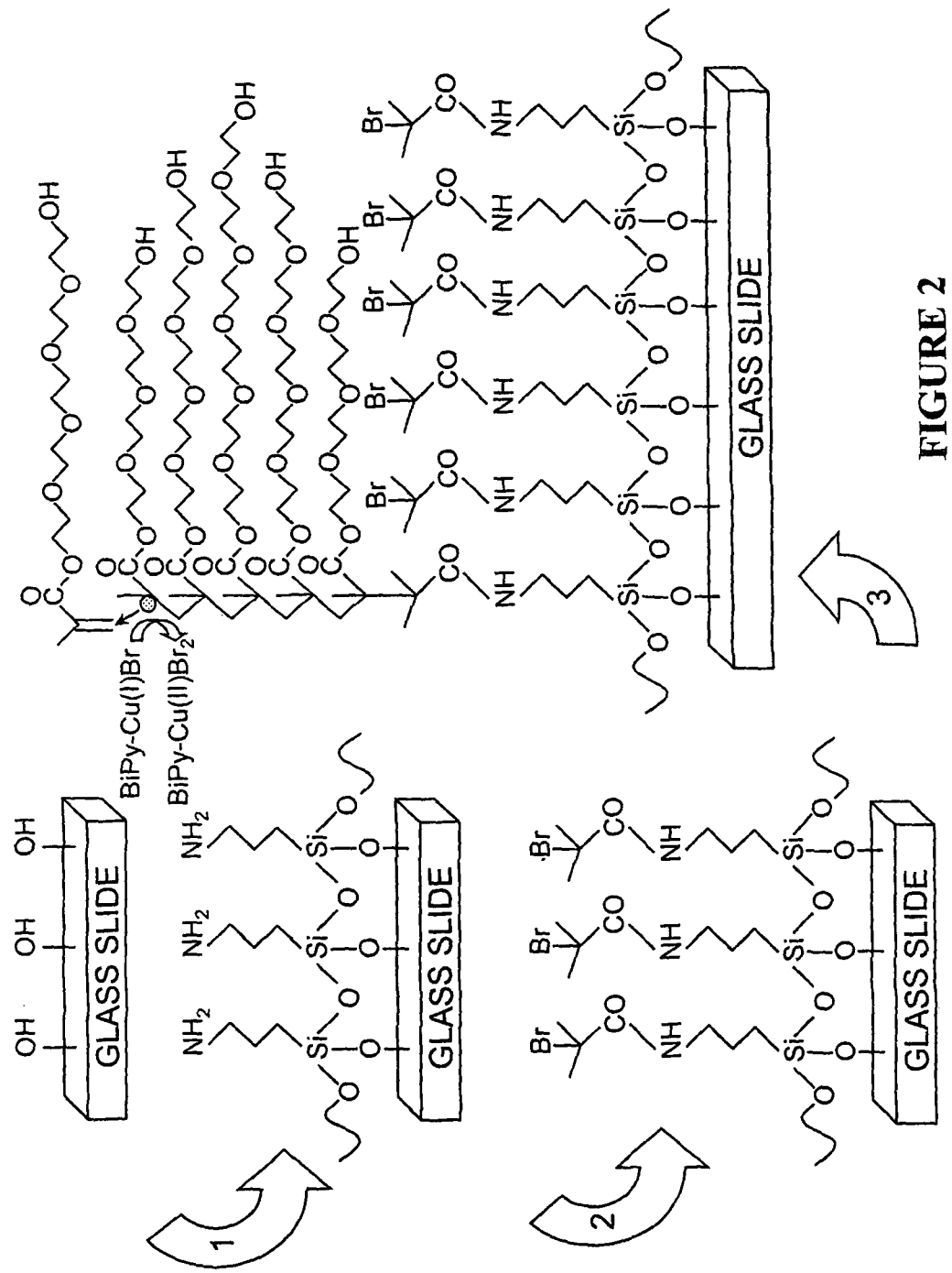
FIG. 2. Synthesis of POEGMA brushes on glass via SI-ATRP. Cleaned slides were functionalized with APTES in step 1, and modified to present an ATRP initiator in step 2. Slides were then immersed in a polymerization solution in step 3 to synthesize surface tethered brushes of POEGMA.

We chose to use a poly(oligo(ethylene glycol) methacrylate) (POEGMA) polymer brush as the microarray substrate because it can be conveniently grown on glass as a high-density brush that limits protein adsorption.[5] The procedure (SI) used to grow the POEGMA brushes on glass is summarized in FIG. 2. Ellipsometry in air of POEGMA brushes grown on oxidized silicon wafers under identical conditions indicated a POEGMA thickness of 105±2 nm.

A non-contact PerkinElmer Piezorray was used to print Ab microarrays onto POEGMA substrates at room temperature and humidity using coated slides that had been stored on the benchtop in a closed container for up to two months (substrate storage time had no observed effect on assay performance).

Figure 3:
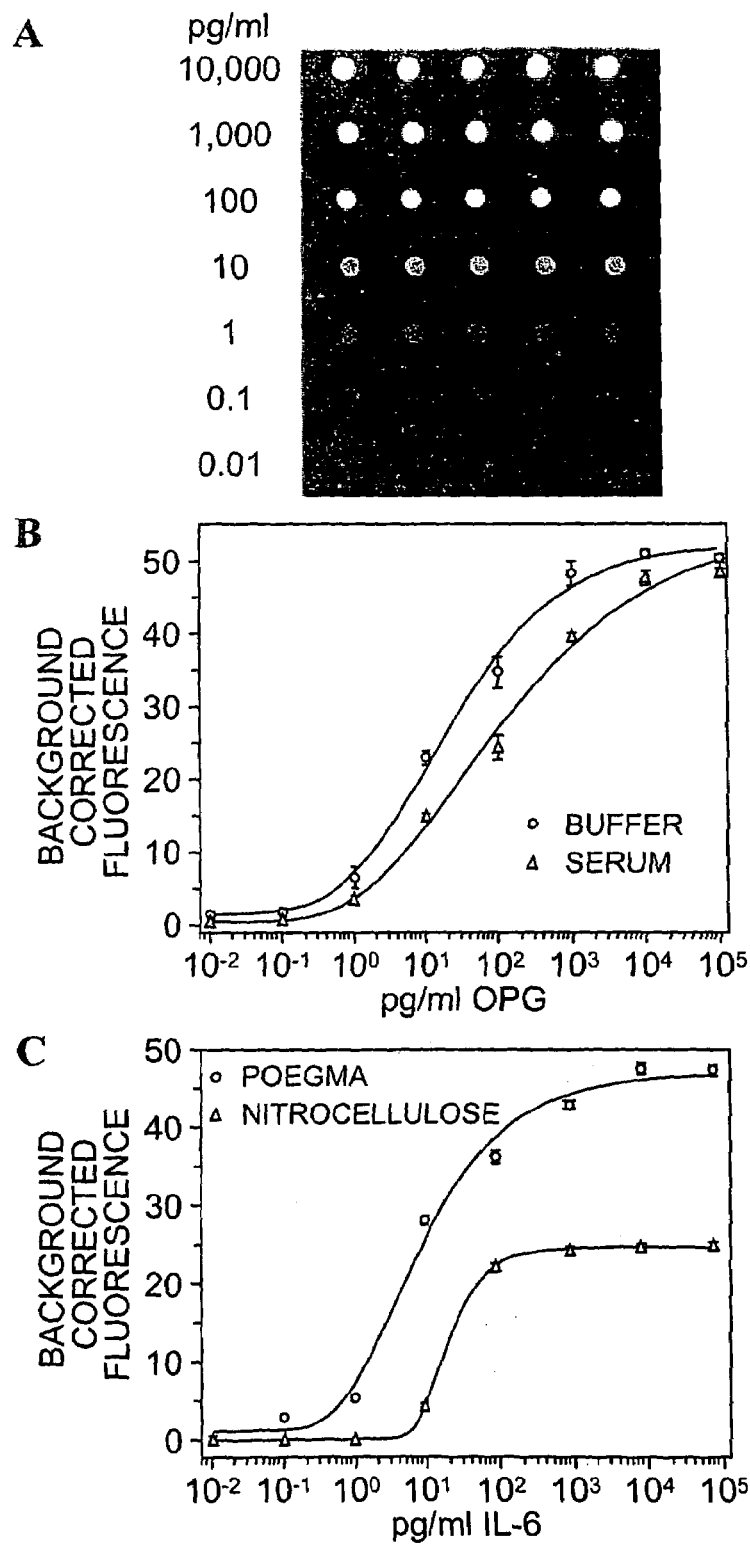
FIG. 3. (A) Example of signal and background intensities in an array used for generation of IL-6 dose response curves (B) Dose response curves of OPG in buffer and serum on POEGMA. (C) Dose response curves of IL-6 in serum on POEGMA and nitrocellulose. In B and C, the Y-axis shows the average background subtracted fluorescence intensity in printed spots and the X-axis shows analyte concentration in solution. Error bars represent one standard deviation.

Antibodies for IL-6 and Osteoprotegerin (OPG) (R&D Systems) were printed from 50 μg/mL solutions and allowed to non-covalently absorb into the 100 nm thick polymer brush. After printing, drying of the spots was facilitated by placing the printed slides under vacuum. This printing and drying process provides stable immobilization of antibody, as arrayed spots of Cy-5 labeled goat anti-rabbit IgG (Jackson) were still visible after high power sonication in a 1% Tween-20 solution (SI). An advantage of this approach over chemical activation of the POEGMA brushes and subsequent covalent attachment[6] is the extreme simplicity of the process, as no slide activation/deactivation steps are required. Non-covalent immobilization via dehydration resulted in equivalent levels of immobilized capture antibody when compared to covalent immobilization via disuccinimidyl carbonate (DSC) and carbonyldiimidazole (CDI) activation procedures (SI). A large increase in background was observed by printing on CDI-activated POEGMA, presumably because of incomplete deactivation of the surface after printing (SI), which highlights another important advantage of printing directly on the polymer brush as opposed to covalent coupling. Furthermore, we found that drying the arrays after printing does not prevent the recognition of analytes by the capture antibodies, nor does it result in bleeding of the spots upon subsequent exposure to liquids during the interrogation of the arrays (FIG. 3a). We hypothesize that the 100 nm thick POEGMA brush functions as a quasi-3D hydrogel that retains sufficient interfacial water, even during macroscopic drying of the printed arrays, to allow retention of antibody structure and hence function—future experiments will test this hypothesis. After printing the capture antibodies, the arrays were stored in vacuum for eventual use in protein assays. Storage time of the Ab arrays from 24 h to two weeks had no obvious effect on array activity. An example of this observation can be seen in FIG. 3b—arrayed slides used to produce the two dose response curves were printed simultaneously, however the assays in buffer preceded the assays in serum by two weeks.

IL-6 and OPG Ab arrays were used to directly probe a dilution series of analyte-spiked PBS and serum (assay details below). To compare the performance of these arrays against a commonly used array material, we also printed the same Ab arrays on commercially available nitrocellulose membranes (Whatman), which are used because of their ability to provide high print densities of the capture antibody and hence high signal. Assays on nitrocellulose substrates were performed according to the manufacturer's suggested protocol.

The fluorescence intensity after scanning and background subtraction for different concentrations of IL-6 as a function of analyte concentration in serum are shown in FIG. 2C for nitrocellulose and POEGMA. The data clearly show that the fluorescence signal from the printed capture Ab spots on nitrocellulose are only visible to a concentration of 10 pg/ml, while the signal on POEGMA is clearly visible down to a concentration of 100 fg/ml. Furthermore, despite the incubation and rinse steps, there was no bleeding of the spots (FIG. 3A), which confirmed the stable immobilization of the capture antibody. The image in FIG. 3A also shows that the POEGMA matrix retains its ability to resist non-specific protein adsorption throughout the entire array fabrication and assay process-fluorescence intensities of the background areas surrounding printed spots measured prior to the assay show no increase in intensity upon completion of the procedure (the only background fluorescence detected on the POEGMA substrates is due to the autofluoresence of the glass slide). This elimination of background signal allows the POEGMA substrates to achieve LODs (signal was considered significant if greater than three standard deviations above the average of the same Ab spots exposed to non-spiked serum) that are up to two orders of magnitude more sensitive when compared to traditional nitrocellulose substrates, as shown by the dose-response curves in FIG. 3C.

The POEGMA substrates also provide an improved dynamic range and can quantify protein concentration across six orders of magnitude, as seen in the dose response curves in FIG. 2 and summarized in Table 1. OPG dose response curves in buffer and serum are shown in FIG. 2B to illustrate the important point that the Ab arrays on POEGMA have virtually identical LODs in buffer and serum. This is in contrast to most other fluorescence immunoassays, where the LOD is typically orders of magnitude greater in complex physiological solutions containing high concentrations of extraneous proteins when compared to LODs determined in buffer.

TABLE 1

Limits of Detection (LOD) and Dynamic Ranges of Serum-Based Microarray Assays on POEGMA

| Analyte | LOD | Dynamic Range |
| --- | --- | --- |
| IL-6 | 100 fg/mL | 100 fg/mL-10 ng/mL |
| IL-1β | 100 fg/mL | 100 fg/mL-10 ng/mL |
| TNF-α | 100 fg/mL | 100 fg/mL-10 ng/mL |
| IL-8 | 100 fg/mL | 100 fg/mL-10 ng/mL |
| OPG | 1 pg/mL | 1 pg/mL-10 ng/mL |

In conclusion, we have demonstrated antibody arrays on POEGMA brushes with several significant features: first, the direct physical printing of the capture Abs provides a simple and robust procedure for the stable immobilization of the capture Abs that avoids the need for chemical activation and deactivation of the surface. Second, the printed microarrays have a practical shelf-life of at least several weeks with no loss in performance. Third, antibody arrays printed on the POEGMA brushes require during interrogation of the array, which simplifies the assay. Finally, the resistance of the POEGMA brushes to protein adsorption from solution eliminates background noise in the microarrays stemming from adventitious protein adsorption and leads to LODs as low as 100 fg/mL in serum (which corresponds to 4 fM for IL-6). The femtomolar LODs in serum and the wide dynamic range suggest that these microarrays will be useful for the quantification of low abundance protein biomarkers directly from complex mixtures with minimal sample pre-processing.

Methods:

Synthesis of POEGMA Surfaces:

The POEGMA brushes were fabricated on glass as follows (FIG. 2, all chemicals purchased from Sigma): first, glass slides (VWR) were cleaned in a solution of 3:1 $H_2SO_4$:$H_2O_2$ for 30 minutes. After rinsing with deionized $H_2O$ and drying, the cleaned slides were immersed in 10% aminopropyltriethoxysilane (APTES) in ethanol for 30 min and were then rinsed with ethanol and dried at 120° C. for 3 h (step 1). Slides were then immersed in a solution of 1% bromoisobutyryl bromide and 1% triethylamine in dichloromethane for 30 min, rinsed with dichloromethane and ethanol, and blown dry with $N_2$ (step 2). Slides were then immersed for 12 h in a degassed polymerization solution of 5 mg/mL Cu(I)Br, 12 mg/mL bipyridine and 300 mg/mL oligo(ethylene glycol) methacrylate under argon (step 3). Finally, slides were rinsed with deionized $H_2O$ and blown dry with $N_2$.

Figure 4:
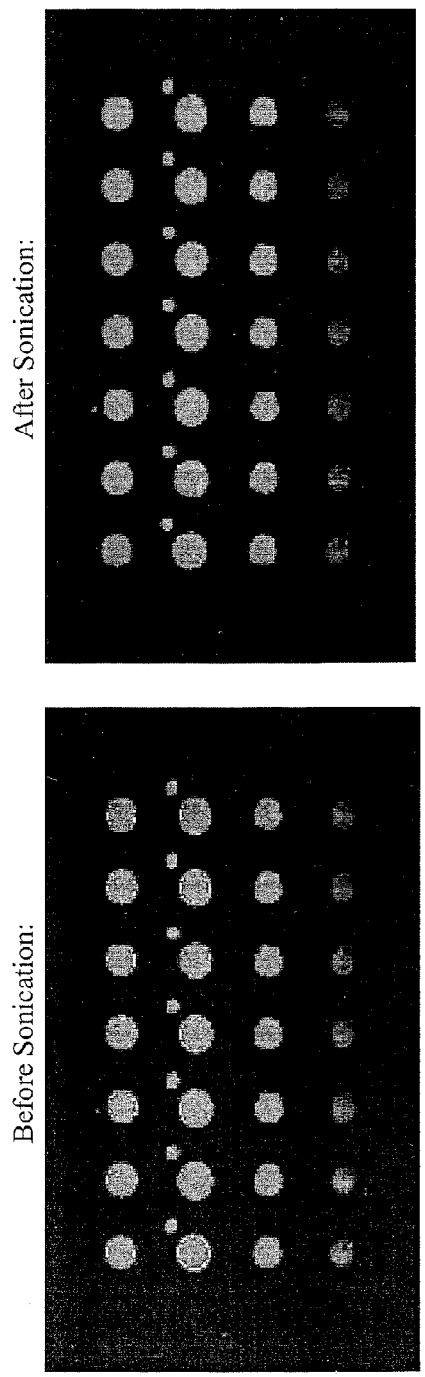
FIG. 4. Cy-5 labeled goat anti-rabbit IgG (Jackson) printed on POEGMA substrates prepared for both covalent and non-covalent attached to produce arrays.

Antibody Immobilization:

Cy-5 labeled goat anti-rabbit IgG (Jackson) was printed on POEGMA substrates to produce arrays seen in FIG. 4. The arrays were dehydrated for 24 hours to promote immobilization and then subjected to high power sonication for 10 minutes in a 1% Tween-20 PBS solution.

Figure 5:
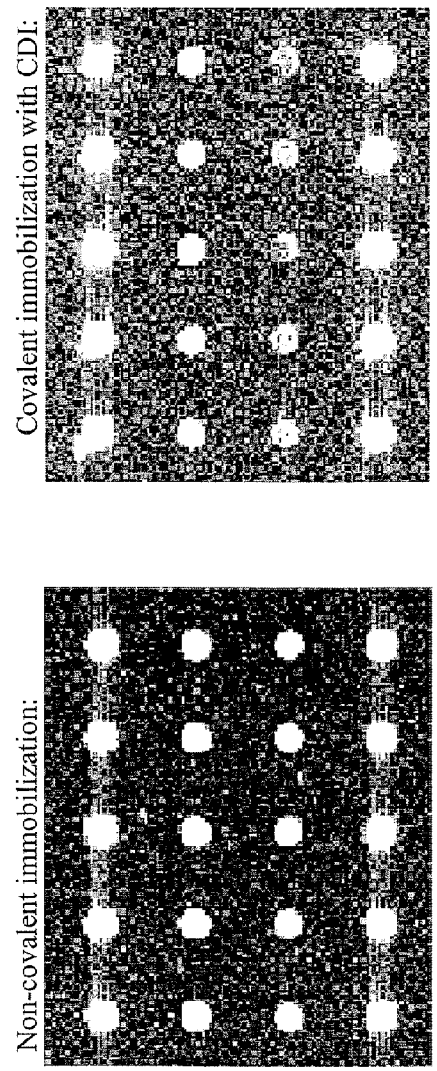
FIG. 5. Incubation of the arrays of FIG. 4 with Cy5 labeled goat anti-rabbit IgG yielded similar spot intensities for both immobilization methods, however, background levels on the activated slides (covalently coupled arrays) increased dramatically.

Covalent vs. Non-Covalent Attachment:

Identical arrays of mouse anti-goat IgG were printed onto unmodified POEGMA substrates as well as substrates that had been activated with either disuccinimidyl carbamate (DSC) or carbonyldiimidazole (CDI). Subsequent incubation with Cy5 labeled goat anti-rabbit IgG yielded similar spot intensities for both immobilization methods, however, background levels on the activated slides increased dramatically, as shown in FIG. 5. We suggest that the use of ethanolamine to deactivate unused conjugation sites, and the subsequent incorporation of large numbers of amide bonds into the POEGMA layer, as well as residual reactive groups, led to the increase in non-specific protein adsorption and coupling in subsequent steps.

CDI Activation Protocol:

Slides were immersed in a 0.5M solution of CDI in dry dioxane for two hours at 37° C. with stirring and then rinsed with dry dioxane, dried, and used immediately for printing.

DSC Activation Protocol:

Slides were immersed in a solution of 0.6M DSC and 0.6M 4-(dimethylamino)pyridine in dry acetone for 6 hours with stirring and then rinsed with dry acetone, dried, and used immediately for printing.

Deactivation Protocol:

Printed slides were immersed in a 0.1M Na Borate buffer at pH 8.5 for 1 hour, and were then transferred to a 0.1M Na Borate buffer at pH 8.5 with 1M ethanolamine for 1 hour.

Multiplexed sandwich immunoassay details: Arrays were first incubated with a dilution series of 100 ml of analyte-spiked PBS or serum for 2 h with stirring, followed by 100 ml 1 mg/ml biotinylated secondary antibody in PBS with 1% (w/v) BSA for 1 h. Finally, the arrays were developed by incubation in 100 ml of 1 µg/ml streptavidin-Cy5 for 30 min, and then scanned with an Axon Genepix 4200 fluorescence microarray scanner. After each incubation step, arrays were washed twice for 30 s with 1% BSA (w/v) and 0.1% (w/v) Tween-20 in PBS.

REFERENCES 1 a) Schena et al, 1995 *Science* 270: 467-470 b) Mantripragada K et al, 2004 *TIG* 20: 87-94 c) Stoughton R B 2005 *Annu Rev Biochem* 74: 53-82

2 a) Angenendt, P., Lehrach, H., Kreutzberger, J., et al. 2005 *Proteomics* 5, 420-425 b) Haab, B. B. 2003 *Proteomics* 3, 2116-2122. c) Kingsmore, S. F. 2006 *Nature Rew Drug Discov* 5, 310-320. d) Kusnezow, W., Hoheisel, J. D. 2003 *J Mol. Recognit* 16: 165-176 e) Macbeath, G. 2002 *Nature Genetics* 32, 526-532 d) Pavlickova, P., Schneider, E. M., and Hug, H. 2004 *Clin Chim Acta* 343, 17-35. e) Wilson, D. S., and Nock, S. 2003 *Angew Chem* 42, 494-500. f) Wingren, C., and Borrebaeck, C. A. K. 2004 *Expert Rev Proteomics* 1, 355-364. g) Wingren, C., and Borrebaeck, C. A. K. 2006 Omics 10, 411-427 h) Zhu, H., Bilgin, M., and Snyder, M. 2003 *Annu Rev Biochem* 72, 783-812.

3 a) Kusnezow, W., Syagailo, Y. V., Ruffer, S., Klenin, K., Sebald, W., Hoheisel, J. D., Gauer, C., and Goychuk, I. 2006 *Proteomics* 6, 794-803 b) Kusnezow, W., Syagailo, Y. V., Goychuk, I., Hoheisel, J. D., and Wild, D. G. 2006 *Expert Rev. Mol Diagn* 6, 111-124

4 a) Selby C 1999 *Ann Clin Biochem* 36, 704-21 b) Wood W G 1991 *Scand J Clin Lab Invest Suppl* 205, 105-112

5 a) Ma H W, Li D J, Sheng X, et al. 2006 *Langmuir* 22: 3751-3756 b) Brown A A, Khan N S, Steinbock L, et al. 2005 *Eur. Polym. J.* 41: 1757-1765 c) Tugulu, S., Klok, H A 2008 *Biomacromolecules*, 9: 906-912

6 a) Tugulu S, Arnold A, Sielaff I, et al. 2005 *Biomacromolecules* 6: 1602-1607 b) Lee B S, Chi Y S, Lee K B, et al. *Biomacromolecules* 8: 3922-3929

The foregoing is illustrative of the present invention, and is not to be construed as limiting thereof. The invention is defined by the following claims, with equivalents of the claims to be included therein.

That which is claimed is:

1. A biomolecular detector, comprising:
    (a) a substrate having a surface portion;
    (b) a linking layer on said surface portion;
    (c) a polymer layer formed on said linking layer, said polymer comprising monomeric units, with each of said monomeric units comprising a monomer core group having at least one protein-resistant head group coupled thereto, to thereby form a brush molecule on said surface portion;
    said brush molecule comprising a stem formed from the polymerization of said monomer core groups, and a plurality of branches formed from said head group projecting from said stem; and
    (d) a first member of a specific binding pair directly non-covalently bound to said polymer layer; wherein said first member is bonded to said polymer layer at a density of from 1 milligram per meter$^2$ to 50 grams per meter$^2$.

2. The detector of claim 1, wherein said first member is a protein, peptide, or nucleic acid.

3. The detector of claim 1, wherein said first member is an antibody.

4. The detector of claim 1, wherein said surface portion comprises a material selected from the group consisting of metals, metal oxides, semiconductors, polymers, silicon, silicon dioxide, and composites thereof.

5. The detector of claim 1, wherein said surface portion comprises silicon dioxide or gold.

6. The detector of claim 1, wherein said linking layer is continuous.

7. The detector of claim 1, wherein said linking layer is patterned.

8. The detector of claim 1, wherein said linking layer comprises a silane layer or a self-assembled monolayer.

9. The detector of claim 1, wherein said brush molecule is from 5 to 200 nanometers in length.

10. The detector of claim 1, said brush molecule formed on said surface portion at a density from 10 to 500 milligrams per meter$^2$.

11. The biomolecular detector of claim 1, wherein: said first member of said specific binding pair is directly non-covalently bound to said polymer at a discrete probe location, said biomolecular detector further comprising:
    (e) a plurality of additional first members of a specific binding pairs directly non-covalently bound to said polymer layer at a plurality of additional discrete probe locations to thereby form an array thereon.

12. The biomolecular detector of claim 11, wherein said array has a density of 5 to 10,000 discrete probe locations per cm$^2$ thereon.

13. The biomolecular detector of claim 11, wherein said array has a density of 10,000 to 1 million discrete probe locations per cm$^2$ thereon.

14. The biomolecular detector of claim 11, wherein said array has a density of 1 million to 1 billion discrete probe locations per cm² thereon.

15. The detector of claim 1 sealed in macroscopically dry form in a container.

16. A biomolecular detector, comprising:
(a) a substrate having a surface portion;
(b) a linking layer on said surface portion, wherein said linking layer is patterned;
(c) a polymer layer formed on said linking layer, said polymer comprising monomeric units, with each of said monomeric units comprising a monomer core group having at least one protein-resistant head group coupled thereto, to thereby form a brush molecule on said surface portion;
said brush molecule comprising a stem formed from the polymerization of said monomer core groups, and a plurality of branches formed from said head group projecting from said stem;
(d) an antibody directly non-covalently bound to said polymer layer; and
(e) a plurality of additional antibodies directly non-covalently bound to said polymer layer at a plurality of additional discrete probe locations to thereby form an array thereon; wherein said array has a density of 10,000 to 1 million discrete probe locations per cm² thereon.

17. The detector of claim 16 sealed in macroscopically dry form in a container.

18. The detector of claim 1 having a limit-of-detection of 100 fg/mL to 10 ng/mL in either serum or buffer.

19. The detector of claim 16 having a limit-of-detection of 100 fg/mL to 10 ng/mL in either serum or buffer.

20. A biomolecular detector, comprising:
(a) a substrate having a surface portion;
(b) a linking layer on said surface portion, wherein said linking layer is patterned;
(c) a polymer layer formed on said linking layer, said polymer comprising monomeric units, with each of said monomeric units comprising a monomer core group having at least one protein-resistant head group coupled thereto, to thereby form a brush molecule on said surface portion;
said brush molecule comprising a stem formed from the polymerization of said monomer core groups, and a plurality of branches formed from said head group projecting from said stem;
(d) an antibody directly non-covalently bound to said polymer layer; and
(e) a plurality of additional antibodies directly non-covalently bound to said polymer layer at a plurality of additional discrete probe locations to thereby form an array thereon; wherein said array has a density of 10,000 to 1 million discrete probe locations per cm² thereon; and wherein the detector is sealed in macroscopically dry form in a container with a shelf life of at least 2 to 4 months when stored at a temperature of 25° C.

21. The detector of claim 1, wherein the first member of a specific binding pair absorbs into said polymer layer.

22. The detector of claim 16, wherein the antibody absorbs into said polymer layer.

23. The detector of claim 1, wherein the first member of a specific binding pair is printed onto said polymer layer.

24. The detector of claim 16, wherein the antibody is printed onto said polymer layer.

* * * * *

UNITED STATES PATENT AND TRADEMARK OFFICE
CERTIFICATE OF CORRECTION

| | | |
|---|---|---|
| PATENT NO. | : 8,796,184 B2 | Page 1 of 1 |
| APPLICATION NO. | : 12/405300 | |
| DATED | : August 5, 2014 | |
| INVENTOR(S) | : Chilkoti et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 979 days.

Signed and Sealed this
Fourth Day of August, 2015

Michelle K. Lee
*Director of the United States Patent and Trademark Office*